United States Patent [19]

Ku

[11] Patent Number: 5,053,453

[45] Date of Patent: Oct. 1, 1991

[54] THROMBORESISTANT MATERIALS AND METHODS FOR MAKING SAME

[75] Inventor: Cecilia S. L. Ku, Lake Forest, Ill.

[73] Assignee: Baxter International Inc., Deerfield, Ill.

[21] Appl. No.: 641,320

[22] Filed: Jan. 15, 1991

Related U.S. Application Data

[63] Continuation of Ser. No. 265,604, Nov. 1, 1988, abandoned.

[51] Int. Cl.[5] .................... C08G 63/48; C08G 63/91
[52] U.S. Cl. .................................. 525/54.1; 530/811; 530/812; 530/813; 530/814; 530/815; 530/816; 523/112
[58] Field of Search ............... 525/54.1; 530/324, 810, 530/811, 812, 813, 814, 815, 816; 523/112; 536/21

[56] References Cited

U.S. PATENT DOCUMENTS

| | | | |
|---|---|---|---|
| 4,415,490 | 11/1983 | Joh | 525/54.2 |
| 4,521,564 | 6/1985 | Solomon et al. | 523/112 |
| 4,526,714 | 7/1985 | Feijen et al. | 525/54.1 |
| 4,600,652 | 7/1986 | Solomon et al. | 523/112 |
| 4,617,271 | 10/1986 | Nambu | 435/182 |
| 4,725,279 | 2/1988 | Woodroof | 523/112 |
| 4,734,097 | 3/1988 | Tanabe et al. | 524/557 |
| 4,742,157 | 5/1988 | Yamanaka et al. | 530/350 |
| 4,746,731 | 5/1988 | Bohn et al. | 530/350 |

FOREIGN PATENT DOCUMENTS 0200655 11/1986 European Pat. Off. .
0357242 3/1990 European Pat. Off. .

OTHER PUBLICATIONS

Ito et al., "Immobilization of CGP39393 (Hirudin), a Specific Thrombin Inhibitor, on Artificial Surfaces", Circulation Supplement, Abstracts from the 61st Scientific Sessions of the American Heart Association, Part II, vol. 78, No. 4, Oct. 1988.

*Primary Examiner*—Nathan M. Nutter
*Attorney, Agent, or Firm*—Sarah E. Bates; Charles R. Mattenson; Paul C. Flattery

[57] ABSTRACT

Thromboresistant materials are disclosed comprising hirudin or hirudin derivatives covalently linked to support materials such that the resultant composition has substantially the same biological activity as hirudin. Methods for making such compositions are also disclosed.

27 Claims, 2 Drawing Sheets

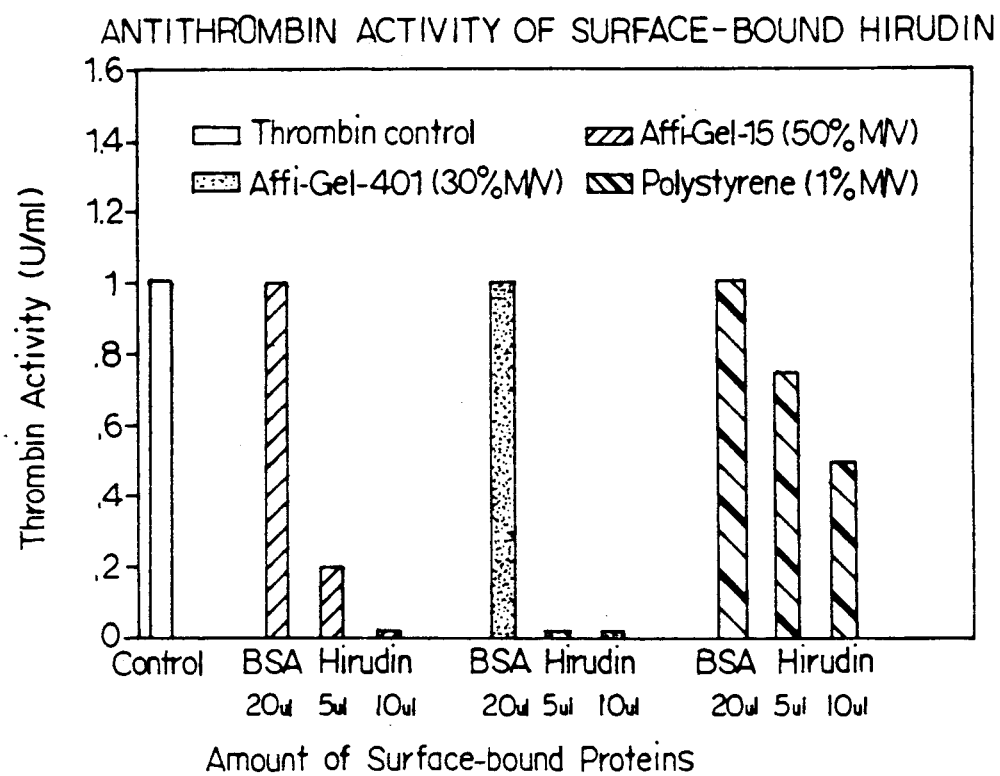
FIGURE 1  Inhibition of the amidolytic activity of thrombin by surface-bound hirudin.
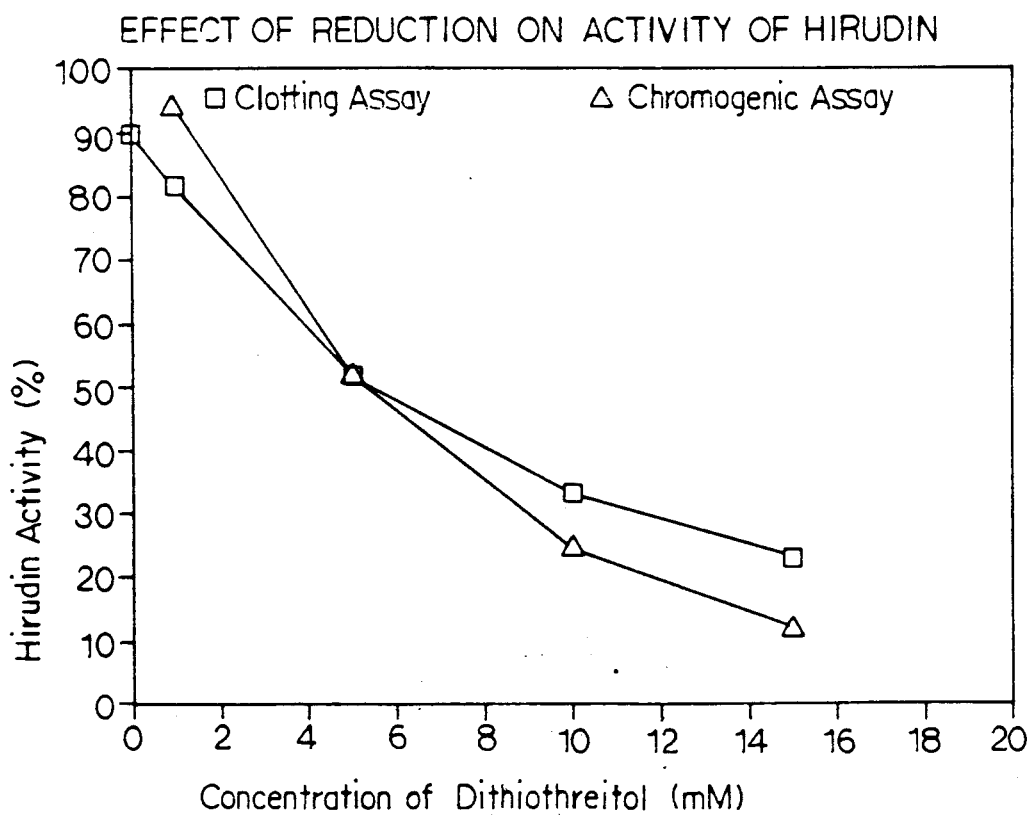
FIGURE 2  Effect of the reduction on the biological activities of hirudin.

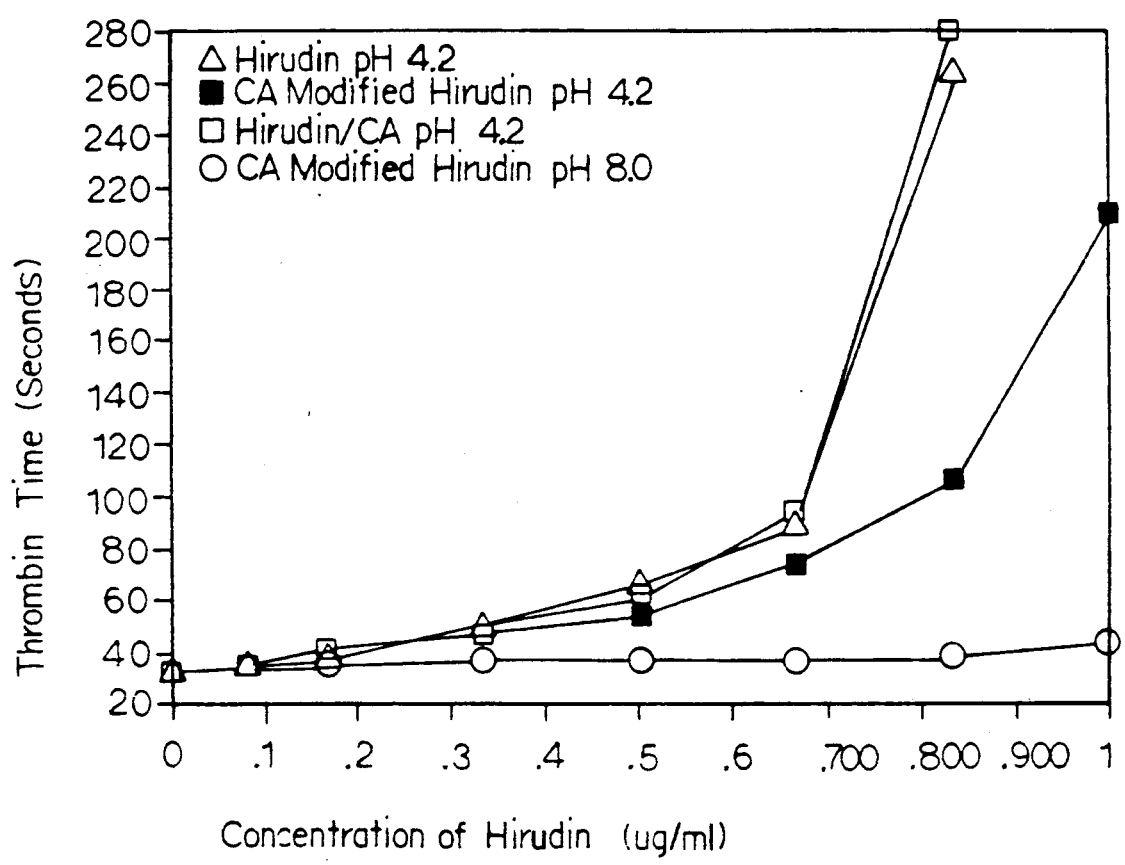
FIGURE 3  Reversible blocking of the anti-thrombotic activity of hirudin (0.14 uM) by the treatment of citraconic anhydride (11.0 uM).

THROMBORESISTANT MATERIALS AND METHODS FOR MAKING SAME

This is a continuation of application Ser. No. 7/265,604, filed on Nov. 1, 1988, now abandoned.

This invention relates to thromboresistant materials, and particularly relates to polymeric materials to which hirudin or hirudin derivatives are covalently linked. The invention is further related to novel methods for producing such thromboresistant materials.

Thrombosis has been a major problem in the development and use of medical devices such as blood collecting and processing systems. As blood comes into contact with foreign surfaces both humoral and cellular alterations occur. To improve the biocompatibility of materials for use in such devices research has focused on immobilization of anticoagulants and biologically active antithrombogenic substances onto the surface of polymers.

One such anticoagulant, heparin, is a mucopolysaccharide which has been used extensively in clinical practice to treat various thrombotic disorders. The therapeutic use of heparin is often complicated by side effects such as prolonged bleeding times. Heparin and its derivatives have been coupled to polymers in an attempt to provide biocompatible surfaces and to reduce the dose of systemic administration of heparin. However, the long term effect of these biomaterials is unknown.

For example, U.S. Pat. Nos. 3,511,684, 3,585,647, 4,254,180, 4,676,974 and 4,678,660 disclose methods for adsorbing or ionically binding heparin to a surface. U.S. Pat. Nos. 4,526,714, 4,634,762, 4,678,671 disclose a method for covalently bonding heparin to a protein to produce a coating for surfaces.

U.S. Pat. No. 4,415,490 discloses a nonthrombogenic material consisting of heparin covalently bound to a polymeric substrate. U.S. Pat. No. 4,326,532 discloses medical materials having antithrombogenic surfaces comprising a polymeric substrate coated with chitosan to which is appended an antithrombotic agent. U.S. Pat. Nos. 4,521,564, 4,600, 652, and 4,642,242 disclose antithrombogenic polyurethane polymers comprising polyurethane materials to which antithrombogenic materials are covalently bound.

Japanese Patent Application 56-150549 discloses an antithrombogenic medical material comprising a hydrogel. In one embodiment the material comprises a hydrogel containing noncovalently bound heparin. Hirudin is also mentioned in the reference as an anticoagulant.

European Patent Application No. 0 200 655 discloses a method for treating materials for use in medical devices in which the surface is treated with a wetting solution of a paladium or rhodium salt and then treated with an anticoagulant such as heparin or hirudin under conditions to cause peptide hydrogen ionization forming ionically bound coatings.

An alternative anticoagulant to heparin is hirudin, a naturally occurring anticoagulant originally isolated from the salivary glands of the medicinal leech. It is a potent and specific thrombin inhibitor with a $K_d$ of approximately $10^{-11}$ M/L. Biochemically and pharmacologically, hirudin presents substantial advantages over heparin. For anticoagulant activity heparin requires the presence of either antithrombin III or heparin cofactor II as a cofactor. It is neutralized by the presence of platelet factor 4; it activates platelets; and it is commonly associated with prolonged bleeding and thrombocytopenia. Hirudin, on the other hand, requires no cofactors, is not neutralized by platelet factor 4, does not activate platelets, has seldomly been associated with prolonged bleeding times and does not cause thrombocytopenia. In addition hirudin has been shown to be five to ten times more effective than heparin in preventing microthrombosis.

Attempts to utilize hirudin for the formation of antithrombogenic, nonthrombogenic or thromboresistant materials have presently been limited to ionic binding of the hirudin molecule to surfaces. These processes are inherently disadvantageous because the hirudin molecules disassociate from the surfaces in relatively short periods of time reducing the longterm thromboresistance of the material.

In the present invention, a thromboresistant material is provided which comprises a support material having functional groups to which hirudin or a hirudin derivative is covalently bound such that the resulting material has substantially the same biological activity as hirudin. The support materials can comprise naturally and synthetically occurring polymers as well as membranes, tissues and organs. The hirudin or hirudin derivative can be directly coupled to the functional group of the support material through the functional groups of its amino acid residues, or it can be coupled indirectly using a linking group. One example of such a linking group would be a bifunctional reagent.

The thromboresistant materials of the present invention can be produced by the direct coupling of the hirudin or hirudin derivative to a functional group of a suitable support material using anhydrous or hydrous coupling reactions. Thromboresistant materials can also be produced by first attaching a linking group to either the support material or the hirudin or hirudin derivative and then coupling the modified material or protein through the linking group to the hirudin or hirudin derivative or the support material. The active sites of the hirudin or hirudin derivative can be protected during the coupling reactions to prevent reduction of activity of the resulting material. In addition, the functional groups of the support material, or the functional groups of the amino acids of the hirudin or hirudin derivative, can be modified to enhance the efficiency or selectivity of the coupling reaction.

BRIEF DESCRIPTION OF THE DRAWINGS

FIG. 1 illustrates inhibition of amidolytic activity of thrombin by surface-bound hirudin.

FIG. 2 illustrates the effect of reduction on the biological activity of hirudin.

FIG. 3 illustrates the effect of reversible blocking of the antithrombotic activity of hirudin using treatment with citraconic anhydride.

For the purposes of this specification, biological activity shall be defined to mean antithrombotic activity. Antithrombotic activity can include, but is not limited to, the ability to inhibit thrombin-catalyzed fibrin clot formation, the amidolytic activity of thrombin through binding of thrombin, or both. Thromboresistant materials which have substantially the same biological activity as hirudin shall mean any material displaying at least about 10% of the antithrombotic activity of unbound native hirudin.

Although this discussion is phrased primarily in terms of the antithrombotic activity of hirudin and the resultant materials of this invention, it should be recognized that hirudin has been shown to have anti-inflammatory, antibiotic and diuretic properties as well. The thromboresistant materials of the instant invention may also be anti-inflammatory, antibiotic or have diuretic properties and can therefore also be utilized as biocompatible materials in general taking advantage of such properties.

The thromboresistant materials of this invention comprise support materials having surfaces to which hirudin or hirudin derivatives are covalently attached in such a manner to substantially preserve the biological activity of the hirudin or hirudin derivative.

The materials which are useful in this invention as supports include those materials which are useful in the production and use of medical products, systems and devices. Support materials include any materials which contain functional groups such as hydroxyl groups, carboxyl groups, amino groups, aldehydes, amides, and sulfhydryl groups, and any materials which can be modified to contain such functional groups or to which such functional groups can be attached. Such materials include both naturally occurring, genetically derived and synthetic materials. Such naturally occurring materials can include, but are not limited to, tissues, membranes, organs and naturally occurring polymers. One example of a genetically derived material is poly-beta-hydroxybutyrate. Synthetic materials can include, but are not limited to, polymers and copolymers.

Such naturally occurring, genetically derived and synthetic polymers include, but are not limited to, homo- and copolymers derived from one or more, in any logical and appropriate combination, of the following: 1-olefins, such as ethylene, propylene, 4-methyl-1-pentene, tetrafluoroethylene, hexafluoropropylene, vinylidine difluoride, etc.; vinyl monomers, such as vinyl chloride, vinylacetate, styrene, maleic anhydride, methylmethacrylate, vinyl sulfonic acid, acrylonitrile, vinylene carbonate, acrylamide, etc.; ethers, such as methylene, ethylene, propylene, tetramethylene, 2,6-dimethyl-1,4-phenylene, etc.; esters, such as ethylene-terephthalate, butylene-terephthalate, gamma-caprolactone, beta-butyrolactone, ethylene-adipate, bisphenol A-tere/isophthalate, etc.; carbonates, such as bisphenol A, 4,4-dihydroxybiphenylene, etc.; amides (including ureas and urethanes), such as nylons, proteins, etc.; saccharides, such as glucosamine, glucuronic acid, proteoglycans, saccharides containing sulfates, etc., siloxanes, such as dimethyl siloxane, diphenyl siloxane, trifluoropropyl siloxane, 3-aminopropyl siloxane, carboxypropyl siloxane, polyethyleneiminopropyl siloxane, etc.

Polymers which have been utilized in medical products, systems and devices include, but are not limited to, the following: polyvinylchloride (PVC) mixed with plasticizers (30%-40% ethyl-hexyl phthalate) used for tubes, catheters and blood bags; polyethylene used for catheters; polypropylene used for disposable materials and syringes; polyacrylonitrile (PAN) used for membranes and hollow fibers for use in haemodialysis; poly (hydroxyethyl methacrylate) used for contact lenses; polytetrafluoroethylene (PTFE), polyethylene terephthalate and polyamides used for vascular prostheses; polyurethanes used for artificial hearts and catheters; polydimethylsiloxane used in prostheses, membrane oxygenators, catheters and plastic surgery; polysaccharides such as cellulose and cellulose acetate used in haemodialysis membranes.

Polymers which are useful in this invention can include biodegradable, partially biodegradable and nonbiodegradable polymers. Support materials also include metals which can be oxidized and then functionalized using reagents such as diethylene triamine pentacetic acid anhydride. Other materials which can be utilized as support materials include, but are not limited to, ceramics and glass.

The choice of the material to be used will usually depend primarily upon the function of the medical device or product to be produced. Where synthetic polymers are utilized, the choice of polymer can also be influenced by the preferred coupling site on the hirudin, the method of coupling, and the functional groups of the polymer. For example, polymers which contain hydroxyl groups include, but are not limited to, polyvinyl alcohol copolymers, glass, silica, and polyhydroxyethyl methacrylate. Polymers containing carboxyl groups include, but are not limited to, maleic anhydride copolymers and carboxymethyl cellulose. Polymers which contain amino groups include, but are not limited to, modified silica gel, poly-p-amino styrene, polyethyleneimines and linear, cross-linked and highly branched polymers. Polymers which contain aldehyde groups include, but are not limited to, polymers treated with glutaraldehyde and polysaccharides treated with periodate. Polymers containing sulfhydryl groups include, but are not limited to, acetylmercaptosuccinic acid modified polymers. Other useful polymers include, but are not limited to, modified polymers such as fluoropolymers, polyacrylonitrile and silanes.

Hirudin which can be used in this invention includes native or naturally occurring hirudin, synthetically produced hirudin and hirudin produced utilizing recombinant techniques. Hirudin derivatives useful in this invention include any protein or polypeptide which displays substantially the same antithrombogenic biological activity as hirudin. Such derivatives can include hirudin proteins which have been modified to increase stability, increase antithrombogenic activity, increase thrombin binding activity or otherwise enhance the thromboresistant properties of the resulting material. Hirudin derivatives can also include hirudin molecules and such derivatives which have been further modified to provide convenient coupling sites for the instant invention. Such modifications to the structure of hirudin are preferably made so as not to substantially reduce the biological activity of the molecule, and are preferably made in the N-terminus end region or at the C-terminal end of the molecule as discussed further below. Such derivatives can be derived from native or naturally occurring hirudin; can be synthetically produced; can be produced using recombinant techniques; or can be produced using a combination of biological and chemical processes.

In the instant invention, hirudin or hirudin derivatives are covalently attached to the surface of materials in such a manner that the biological activity of the hirudin is not substantially reduced.

Native hirudin is a protein containing sixty-five amino acids having the following amino acid sequence:

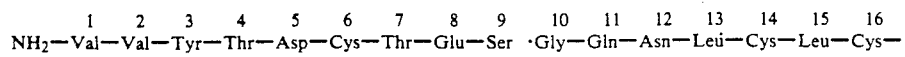

| 17 | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|
| Glu—|Gly—|Ser—|Asn—|Val—|Cys—|Gly—|Gln—|Gly—|Asn—|Lys—|Cys—|Ile—|Leu—|Gly—|Ser—|Asp— |

| 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|
| Gly—|Glu—|Lys—|Asn—|Gln—|Cys—|Val—|Thr—|Gly—|Glu—|Gly—|Thr—|Pro—|Lys—|Pro—|Gln—|Ser— |

| 51 | 52 | 53 | 54 | 55 | 56 | 57 | 58 | 59 | 60 | 61 | 62 | 63 | 64 | 65 |
|---|---|---|---|---|---|---|---|---|---|---|---|---|---|---|
| His—|Asn—|Asp—|Gly—|Asp—|Phe—|Glu—|Glu—|Ile—|Pro—|Glu—|Glu—|Tyr—|Leu—|Gln—COOH |

Native hirudin extracted from leeches has a sulfate group attached to the tyrosine residue at 63. Studies of the structure of hirudin have shown there are three primary functional regions. The first region, the highly anionic region near the C-terminus from amino acid 40 to the C-terminal end is an essential portion of the molecule allowing for the ionic interaction between hirudin and thrombin. The second region, the highly crosslinked region of the molecule containing amino acid residues 6 to 40, is believed to contribute an increased binding affinity of hirudin to thrombin. The third region, the five amino acid residues at the N-terminus, may not be significant for the biological activity of hirudin. This is the preferred region for coupling of the hirudin to material. Analogous regions in hirudin derivatives present preferred coupling sites.

Amino acids most commonly used in coupling proteins to materials include those containing amino, carboxyl, hydroxyl and sulfhydryl groups. Carboxyl group coupling would be less preferred in the instant invention because the C-terminal region is associated with the active site of the hirudin molecule. Amino groups are present in the N-terminal valine and the three lysines at positions 27, 36 and 47. The lysine at 47 is reported to be the primary active center. In some coupling reactions it is preferred that the lysine residues be protected during conjugation. The preferred binding site of hirudin is the N-terminal valine. The histidine residue at 51 and the tyrosines at 3 and 63 are also potential coupling sites. The use of histidine is less preferred because of its proximity to the lysine in the active center. The eight hydroxyls, four serines and four threonines, can also be utilized for coupling to functional groups. Because these eight amino acids are scattered throughout the molecule, such coupling offers less specificity in binding and greater variation in biological activity.

As mentioned above derivatives of hirudin can be prepared which provide coupling sites without compromising the biological activity of the molecule. For example, if alteration of the disulfide bonds near the N-terminus does not substantially affect the activity, the cysteine residue can be modified and coupled to material.

Hirudin or hirudin derivatives can be coupled either directly to the functional groups of the support material or by way of linking groups. Such linking groups, for example, can include chemical groups such as bifunctional reagents, polypeptides such as poly-lysine, proteins and protein segments, and other molecules which are covalently bound to both the support material and the hirudin or hirudin derivative.

The method for producing the thromboresistant materials of this invention generally comprises coupling the hirudin or hirudin derivative by a functional group of an amino acid residue to an active functional group of a support material. The method for coupling is dependent upon several factors including the available functional groups on the support material, the coupling site or sites on the protein, biological activity of the resulting material, selectivity and efficiency of the coupling reaction.

For example, if the coupling sight on the protein, i.e. the amino acid residue, is not in close proximity to the active sight of the protein, i.e. the thrombin binding region, and the support material contains the appropriate active functional groups, the protein may be directly coupled to the support material utilizing reactions known to those skilled in the art. An example of such coupling is the coupling of the amino group on the N-terminal residue to an agarose gel containing N-succinimide esters as functional groups. The coupling reaction can be done under anhydrous or hydrous conditions.

In the alternative, the protein can be coupled to the support material by a linking group. Examples of linking groups which can be used in this invention include, but are not limited to, bifunctional reagents such as bifunctional protein crosslinking reagents, polypeptides, proteins, protein segments, and multifunctional polymers such as polyethyleneimines or dendritic polymers. The choice of a linking group can depend on the coupling site, the functional groups of the support material, biological activity of the resulting material and the efficiency and selectivity of the coupling reaction. For example, the phenolic group of tyrosine can be modified using bifunctional reagents such as N-(4-diazobenzoyl)-N (3-maleimidopropionyl) hydrazine-tetrafluoroborate (DMHT) and N-succinimidyl-3-(2-pyridyldithio) propionate (SPDP) to add a sulfhydryl group for coupling with support materials which have active amino groups. In addition to SPDP, acetylmercaptosuccinic anhydride can be used to introduce sulfhydryl groups to any surfaces containing amino groups (Klotz, I. M. and Stryker, V. H., Biochemical Biophysical Research Communication, vol. 1, pp. 119-123 (1959)).

Conjugates of hirudin and support materials can be made using a variety of bifunctional protein crosslinking reagents. Examples of such reagents include SPDP, bifunctional derivatives of imidoesters such as dimethyl adipimidate and dimethyl suberimidate, active esters such as disuccinimidyl suberate, aldehydes such as glutaraldehyde and glycolaldehyde, bis-azido compounds such as bis-(p-azidobenzoyl) hexanediamine, bis-diazonium derivatives such as bis-(p-diazoniumbenzoyl)-ethylenediamine, diisocyanates such as tolylene-2,6-diisocyanate and tolylene-2,4-diisocyanate, and bis-active fluorine compounds such as 1,5-difluoro-2,4-dinitrobenzene and other reagents such as ethylene glycol/-bis-[succinimidyl succinate], m-maleimido benzoyl sulfasuccinimide, diethylene triamine pentacetic acid anhydride.

Where the biological activity of the protein would be greatly reduced by direct coupling due to steric hindrance, such as coupling at the C-terminal residue, or sticking of the protein to the support material, it can be desirable to use a linking group which would act to space the protein away from the support material. Examples of such linking groups include, but are not limited to, polypeptides, proteins and multifunctional polymers. Such linking groups can also provide multiple sites for attachment of the hirudin or hirudin derivatives to increase the binding efficiency.

During the coupling process it is also possible to protect the active region of the protein, i.e. the thrombin binding region, by protecting the active functional groups of the amino acid residues of the region. For example, studies have suggested that the lysine residue at position 47 might be involved in the biological activity of hirudin. Therefore, this residue can be protected by either protonating the amino groups by adjusting pH or by blocking the amino groups reversibly with such reagents as citraconic anhydride, 3,4,5,6 tetrahydropthalic anhydride, or other reagents known to those skilled in the art.

EXAMPLES

EXAMPLE 1

Native hirudin (approximately 700 ATU/mg, Biopharm, U.K.) was dissolved in HEPES buffer (N-2-hydroxyethylpiperazine-N'-2-ethane-sulfonic acid, 0.1M, pH 7.2) to form solution containing 8 to 10 mg/ml (approximately 6000 ATU/ml). The hirudin solution was kept at 4° C. until use.

Aqueous coupling of hirudin to a derivatized crosslinked agarose gel bead support (Affi-Gel 15, Bio-Rad) was carried out by transferring the desired quantity of agarose gel slurry (approximately 2 ml) to a small sintered glass funnel. Excess supernatant was removed and the gel was washed with three bed volumes of cold (4° C.) deionized water. 0.5 ml of the moist gel was transferred into a test tube containing 1.0 ml of cold hirudin solution in proportions of approximately 0.4 ml gel to 1 ml hirudin solution, i.e. approximately 20–25 mg hirudin per ml of gel. The gel-hirudin mixture was incubated overnight at 4° C. with gentle agitation. After incubation, gel-hirudin was collected by centrifugation at 6,000 rpm for 5 minutes. Gel-hirudin complexes were washed with ten bed volumes of 0.01M phosphate buffered saline, pH 7.0±0.1 (PBS). Remaining active esters were blocked by treatment with 1M glycine ethyl ester, pH 7.8. After an hour incubation at room temperature, excess glycine ethyl ester was removed and the gel was washed three times with ten bed volumes of PBS. Finally, the gel was resuspended in PBS as a 50% w/v suspension and stored at 4° C. until ready for biological assays.

EXAMPLE 2

The anhydrous coupling was conducted by mixing a desired amount of the hirudin solution of Example 1 (8–10 mg/ml) in DMSO (dimethylsulfoxide) with agarose gel Affi-Gel 15 in a ratio of 1 ml of hirudin solution to approximately 0.5 ml of gel. The gel-hirudin mixture was incubated at 4° C. for 4 hours with gentle agitation. After completion of the reaction, excess hirudin was removed and the remaining active esters were blocked by glycine ethyl ester as described in Example 1. Finally, the gel was washed and resuspended in PBS as a 50% w/v suspension and stored at 4° C.

EXAMPLE 3

In order to immobilize hirudin onto a surface containing amino groups via its phenolic group in tyrosine, hirudin was coupled to the polymer using a bifunctional agent in a three-step procedure. First, sulfhydryl groups were introduced to a polystyrene surface containing amino groups. The amino groups were modified using the heterobifunctional reagent SPDP. The 2-pyridyl disulfide structure was introduced into the amino groups of the polystyrene by the reaction of amino groups of the polymer with the N-hydroxysuccinimide ester of the reagent. Specifically, polystyrene-$NH_2$-microparticles (1 ml, 5% w/v) were washed with PBS and resuspended in PBS as a 5% w/v suspension. 0.3 of SPDP (8 mg/ml) ethanol) was added to the suspension. The mixture was incubated at room temperature for two hours. The reaction was terminated by collecting the particles via centrifugation at 3000 rpm for 30 minutes followed by washing the particles twice with 20% ethanol and once with 0.1M acetate buffer, pH 5.0. The modified particles were resuspended in the acetate buffer as a 5% w/v solution. After the completion of the reaction the polystyrene-pyridyl disulfide structure was reduced with 50 mM dithiothreitol (DTT) (Carlson, J., et al: Biochemical Journal, vol. 173, pp. 723–737 (1978)).

In the second step, hirudin was modified utilizing N-(4-diazobenzoyl)-N'-(3-maleimidopropionyl)-hydrazine-tetrafluoroborate (DMHT) to introduce maleimide groups onto the phenolic ring of tyrosine. This modification permitted the conjugation of hirudin to the polystyrene bearing sulfhydryl groups prepared in the first step. The coupling was performed according to the method of Duncan, et al. (Journal of Immunological Methods, vol. 80, pp. 137–140 (1985)). In brief, DMHT was dissolved in DMSO. The resultant DMHT solution (30 mg/ml) was then added to a hirudin solution of 8–10 mg hirudin/ml of 50 mM phosphate buffer, pH 7.8 at 4° C. in a ratio of 10 microliters of DMHT per ml of hirudin solution. After one hour of incubation at 4° C., modified hirudin was separated from the reaction mixture via gel filtration, i.e. Sephadex G-25 equilibrated with 50 mM phosphate buffer, pH 6.5. The fractions containing modified hirudin were pooled and concentrated by lyophilization.

In the final step, the modified hirudin was conjugated to the polystyrene surface containing sulfhydryl groups. Lyophilized hirudin, 3 mg, was reconstituted in 0.5 ml of deionized water. A mixture containing DMHT modified hirudin in phosphate buffer (0.5 to 1.0 ml) and polystyrene-SH beads (0.1 to 0.2 ml, 5% w/v) was gently agitated at room temperature overnight. After washing, the hirudin coated polystyrene was stored in phosphate buffer (50 mM, pH 7.8) as a 1% w/v suspension.

EXAMPLE 4

Hirudin was immobilized through its amino groups to polymer containing sulfhydryl groups via the reagent succinimidyl-4-(N-maleimidomethyl)-cyclohexane-1-carboxylate (SMCC). A hirudin solution of 1 mg hirudin/ml of 0.1M HEPES, pH 7.2, was reacted with SMCC (1 microgram/ml of DMSO) at a molar ratio of 1:10 hirudin to SMCC for one hour at room temperature. The remaining active sites of SMCC were blocked by treatment with 0.1M glycine ethyl ester, pH 7.8, SMCC not coupled to hirudin was removed by gel filtration (Sephadex G-25 equilibrated with HEPES buffer) and the modified hirudin was concentrated resulting in approximately 800 ATU in 0.5 ml. SMCC-activated hirudin, 0.5 ml, was immobilized to the matrix of a sulfhydryl terminal crosslinked agarose gel, Affi-Gel 401 Sulfhydryl Gel (0.3 ml). The coupling reaction was carried out in HEPES buffer overnight at 4° C. The reagent was removed by washing three times with buffers as described previously in Example 3.

The four materials produced in Examples 1 through 4 were tested for thromboresistant properties by testing for the biological activity of the covalently bound hirudin.

Inhibition of the amidolytic activity of thrombin by surface-bound hirudin was measured via a chromogenic assay (S-2238). In this assay, hirudin coated particles, in various amounts, were allowed to react with a fixed quantity of human alpha-thrombin (1 NIH unit). The residual thrombin was quantified by its capacity to cleave a synthetic peptide substrate in a color-producing reaction. The amount of hirudin-coated particles was inversely related to the intensity of color produced in this reaction.

To determine the biological activity of surface-bound hirudin, various amounts of hirudin coated particles (2 microliters to 50 microliters) were placed in the wells of a 96-well microtiter plate. Wells were filled to 50 microliters with a buffer containing 50 mM Tris, 150 mM NaCl, 0.01% human serum albumin. Hirudin-coated particles were incubated with 50 microliters of human alpha-thrombin (2 NIH-U/ml) at room temperature for one hour. A series of human alpha-thrombin standards (0 to 2 NIH U/ml) was included in the assay as a control. The excess thrombin was then measured by the addition of 25 microliters of chromogenic substrate (1-2 mM/L in water). The reaction was carried out at room temperature (or 37° C.) for 10 minutes. The reaction was stopped by the addition of 25 microliters of glacial acetic acid. The supernatant of each well was collected and the color intensity was measured at O.D. 405 nm. The residual thrombin activity of each sample was computed from a standard curve.

The inhibition of thrombin-induced fibrinogen clot activity by surface-bound hirudin was assessed via thrombin clot time. Thrombin clot time measures the direct conversion of fibrinogen to fibrin clot by thrombin. Human Standardized Normal Plasma (Dade Division, Baxter Healthcare Corporation) in 0.1 ml was prewarmed with 0.15 ml of buffer containing 50 mM Tris, 150 mM NaCl (pH 8.0) to 37° C. for 2 minutes. After 2 minutes incubation, 50 microliters of human alpha-thrombin (12 NIH U/ml) was added and the clot time measured by using a fibrometer. For the test samples, various amounts of hirudin-coated particles were preincubated with 50 microliters of human alpha-thrombin 12 NIH U/ml) at room temperature for 10 minutes. After the incubation, the hirudin/thrombin mixture was added to a prewarmed plasma solution containing 0.1 ml of Human Standardized Normal Plasma. Tris/NaCl buffer was added to bring the final volume to 0.3 ml. The thrombin clot time was recorded by a fibrometer.

Finally, based on the fact that thrombin forms an extremely stable one to one complex with hirudin, a direct binding assay was employed to detect surface-bound hirudin. Human alpha-thrombin was iodinated using the iodo-bead method according to the procedure of Markwell (Analytical Biochemistry, vol. 125, pp. 427-432 (1982)). A suspension of hirudin-coated particles (50 microliters) was incubated with desired amount of $^{125}I$-thrombin (specific activity: $2.6 \times 10^6$ cpm/microgram) in phosphate buffered saline containing 0.1% bovine serum albumin (BSA), pH 7.2. After at least a four hour incubation at 4° C., free $^{125}I$-thrombin was removed and thrombin-hirudin coated particles were washed extensively with same buffer. Surface bound $^{125}I$-thrombin was measured. Proper controls were included in each assay to correct for the nonspecific adsorption of $^{125}I$-thrombin. These controls are Affi-Gel 15-BSA; Affi-Gel 15 (blocked, i.e. no reactive groups available); Affi-Gel 15 (unblocked, i.e. with reactive groups); Affi-Gel 401-SMCC-BSA; $NH_2$-polystyrene-BSA and $NH_2$-polystyrene-hirudin.

Results of the first study demonstrate that the surface-bound hirudin of the thromboresistant materials from Examples 1 through 4 maintains its ability to form a complex with thrombin thereby inhibiting thrombin-catalyzed fibrin clot formation (Table 1). Compared with the controls, surface-bound hirudin inhibited thrombin-catalyzed conversion of fibrinogen to fibrin. At least two-fold prolonged thrombin clotting time was observed with Affi-Gel 15 hirudin (20 microliter of 50% w/v), Affi-Gel 401 SMCC hirudin (10 microliter of 30% w/v) and polystyrene DMHT hirudin (2.5 microliter of 1% w/v) were preincubated with fixed amount of human alpha thrombin. Likewise, surface-bound hirudin inhibited the amidolytic activity of thrombin as assessed by the chromogenic assay as shown in FIG. 1. About 90% inhibition was observed when 10 microliter of Affi-Gel 15 hirudin (50% w/v) of Affi-Gel 401 hirudin (30% w/v) was used to neutralize the thrombin activity. A 50% inhibition was obtained when 10 microliter of polystyrene DMHT hirudin (1% w/v) was used. The lower inhibitory activity of polystyrene DMHT hirudin observed in this study could be attributed to the lower concentration of material in the suspension used in the assay. The surface-bound hirudin was monitored by direct binding via $^{125}I$-thrombin as shown in Table 2. Compared with controls, approximately a two-fold and three-fold increase in $^{125}I$ radioactivity was obtained from Affi-Gel 15 hirudin (via anhydrous coupling) and other surface-bound hirudin, respectively. The results from these studies demonstrate that surface-bound hirudin retained its biological activity.

TABLE 1

| EFFECT OF SURFACE-BOUND HIRUDIN ON THROMBIN CLOTTING TIME* | |
|---|---|
| SAMPLES | CLOT TIME (S) |
| CONTROLS | |
| PLASMA ALONE | 49 |
| + AFFI-GEL-15 | 46 |
| + AFFI-GEL-401-SMCC-BSA | 27 |
| + POLYSTYRENE - DMHT-BSA | 47 |
| AFFI-GEL-15-HIRUDIN (AQUEOUS COUPLING) | |
| 10 μL (50% W/V) | 55 |
| 20 μL (50% W/V) | 180 |
| AFFI-GEL-15-HIRUDIN (ANHYDROUS COUPLING) | |
| 10 μL (50% W/V) | 140 |
| 20 μL (50% W/V) | >3,600 |
| AFFI-GEL-401-SMCC HIRUDIN | |
| 5 μL (30% W/V) | 47 |
| 10 μL (30% W/V) | >220 |
| POLYSTYRENE-DMHT-HIRUDIN | |
| 1 μL (1% W/V) | 55 |
| 3 μL (1% W/V) | 127 |

*2 U/ML OF HUMAN α-THROMBIN WAS USED IN THE CLOTTING ASSAY.

TABLE 2

MONITORING SURFACE-BOUND HIRUDIN VIA DIRECT BINDING WITH $^{125}$I-THROMBIN

| SAMPLES | SURFACE-BOUND $^{125}$I-THROMBIN IN CPM/50 μL[1] |
|---|---|
| AFFI-GEL-15-HIRUDIN (AQUEOUS COUPLING) | 4,093 |
| AFFI-GEL-15-BSA | 1,331 |
| AFFI-GEL-15 (BLOCKED)[2] | 1,046 |
| AFFI-GEL-15-HIRUDIN (ANHYDROUS COUPLING) | 2,644 |
| AFFI-GEL-15-BSA | 1,269 |
| AFFI-GEL-15 (UNBLOCKED)[3] | 2,735 |
| AFFI-GEL-401-SMCC-HIRUDIN | 3,204 |
| AFFI-GEL-401-SMCC-BSA | 1,650 |
| POLYSTYRENE-DMHT-HIRUDIN | 6,805 |
| POLYSTYRENE-HSA | 2,171 |
| POLYSTYRENE-HIRUDIN | 2,201 |

[1] 50 μL OF MATRICES SUSPENSION.
[2] AFFI-GEL-15 AGAROSE GEL WAS TREATED WITH 1M CLYCINE ETHYL ESTER. pH 7.8 TO BLOCK THE REACTIVE SITES.
[3] PLAIN AFFI-GEL-15 AGAROSE GEL.

EXAMPLE 5

In order to explore the possibility of a potential coupling site at a disulfide region of the hirudin molecule (e.g. residues 6 through 14, 16 through 22 and 28 through 39) hirudin was reduced with various concentrations of DTT. Hirudin solution, 45 microliters (50 ATU), was incubated with various amounts of DTT ranging from 0 to 15 mM DTT at 37° C., for 5 hours. At the end of the incubation, ten-fold excess of iodoacetic acid was added to each sample. Aliquot samples were tested for hirudin by both clotting and chromogenic assays.

The effect of the reduction on the activity of hirudin was demonstrated in FIG. 2. It appears that the antithrombin activity of hirudin is dependent at least partially upon the structural integrity of one or more of the three disulfide bonds. Nevertheless, the partial reduction of the disulfide bonds, i.e. reduction of less than all three of the disulfide bonds, may create a potential coupling site on the hirudin molecule.

EXAMPLE 6

In order to protect the active lysine residues at position 47, hirudin was modified with citraconic anhydride. Hirudin solution containing 0.14 mM hirudin in 0.2 ml buffer composed of 10 mM phosphate, pH 8.5, was prepared. Citraconic anhydride, 11 micromoles, was added to hirudin solution dropwise over a period of time at room temperature. The pH of the reaction mixture was maintained by the addition of 1M NaOH. The reaction was completed within two hours at room temperature. Excess citraconic anhydride was removed by gel filtration. To remove citraconyl groups from modified hirudin the pH of citraconic anhydride modified hirudin solution was adjusted to pH 4.2 by diluting 20 microliters with 1.9 ml of buffer containing 10 mM acetate, 50 mM NaCl, pH 4.2 and the reaction mixture was incubated for 5 hours at 45° C.

Modification of hirudin with citraconic anhydride via acylation of N-terminal valine and lysine groups reversibly blocked the biological activity of hirudin (FIG. 3), compared with controls (hirudin at pH 4.2; hirudin/citraconic anhydride, pH 4.2). Modification of hirudin with citraconic anhydride abolished the biological activity of hirudin as shown in FIG. 3. Upon removal of citraconyl groups by lowering the pH of the buffer to pH 4.2, about 80% activity was recovered after 5 hours incubation at 45° C. This procedure may be used to protect the active amine groups of hirudin during the immobilization process.

The invention being thus described, it will be obvious that the same can be varied in many ways. Such variations are not to be regarded as a departure from the spirit or scope of the invention and all such modifications are intended to be included within the scope of the claims.

What is claimed is:

1. A thromboresistant material comprising:
   a protein having an amino acid sequence sufficiently complementary to the hirudin binding sites of thrombin so as to have antithrombotic activity;
   covalently bound through a linking group to a support material.

2. The thromboresistant material of claim 1 wherein the support material is a polymer.

3. The thromboresistant material of claim 2 wherein the polymer is a naturally occurring polymer, genetically-derived polymer or synthetic polymer or copolymer.

4. The thromboresistant material of claim 2 wherein the polymer is selected from the group consisting of polyvinylchloride, polyethylene, polypropylene, polyacrylonitrile, poly(hydroxyethyl methacrylate), polytetrafluoroethylene, polyethylene terephthalate, polyamides, polyurethanes, polymethoxysiloxane and polysaccharides.

5. The thromboresistant material of claim 2 wherein the polymer is chosen from the group consisting of polyvinyl alcohol copolymers, glass, silica, polyhydroxyethyl methacrylate, maleic anhydride copolymers, carboxymethyl cellulose, modified silica gel, poly-p-amino styrene, polyethyleneimines, polymers treated with glutaraldehyde, polysaccharides treated with periodate, acetylmercaptosuccinic acid modified polymers, fluoropolymers, polyacrylonitrile and silanes.

6. The thromboresistant material of claim 1 wherein the support material is a membrane, tissue or organ.

7. The thromboresistant material of claim 1 wherein the support material is a metal.

8. The thromboresistant material of claim 1 wherein the support material is a ceramic.

9. The thromboresistant material of claim 1 wherein the support material is a glass.

10. The thromboresistant material of claim 1 wherein the linking group is selected from the group consisting of bifunctional protein crosslinking reagents, polypeptides, proteins, and multifunctional polymers.

11. The thromboresistant material of claim 1 wherein the protein is coupled to the support material by an amino acid residue in the N-terminal region.

12. The thromboresistant material of claim 1 wherein the protein is coupled to the support material by the C-terminal residue.

13. A method for producing a thromboresistant material having substantially the same biological activity as hirudin comprising coupling a protein having substantially the same biological activity as hirudin through a linking group to a support material having active functional groups.

14. The method of claim 13 wherein the support material is a polymer.

15. The method of claim 14 wherein the polymer is a naturally occurring polymer, genetically derived polymer or synthetic polymer or copolymer.

16. The method of claim 14 wherein the polymer is selected from the group consisting of polyvinylchloride, polyethylene, polypropylene, polyacrylonitrile, poly(hydroxyethyl methacrylate), polytetrafluoroethylene, polyethylene terephthalate, polyamides, polyurethanes, polymethoxysiloxane and polysaccharides.

17. The method of claim 14 wherein the polymer is chosen from the group consisting of polyvinyl alcohol copolymers, glass, silica, polyhydroxyethyl methacrylate, maleic anhydride copolymers, carboxymethyl cellulose, modified silica gel, poly-p-amino styrene, polyethyleneimines, polymers treated with glutaraldehyde, polysaccharides treated with periodate, acetylmercaptosuccinic acid modified polymers, fluoropolymers, polyacrylonitrile and silanes.

18. The method of claim 13 wherein the support material is a membrane, tissue or organ.

19. The method of claim 13 wherein the support material is a metal.

20. The method of claim 13 wherein the support material is a ceramic.

21. The method of claim 13 wherein the support material is a glass.

22. The method of claim 13 wherein the linking group is first covalently bound to the protein and then the resulting protein-linking group is covalently bound by a functional group on the linking group end of the protein-linking group to the functional group of the support material.

23. The method of claim 13 wherein the linking group is first covalently bound to the functional group of the support material and then the resulting support material-linking group is covalently bound by a functional group on the linking group end of the support material-linking group to the protein.

24. The method of claim 22 wherein the linking group is selected from the group consisting of bifunctional protein crosslinking reagents, polypeptides, proteins, and multifunctional polymers.

25. The method of claim 13 wherein the protein is coupled to the support material by an amino acid residue in the N-terminal region.

26. The method of claim 13 wherein the protein is coupled to the support material by the C-terminal residue.

27. The method of claim 13 further comprising protecting active sites of in the thrombin binding region of the protein prior to coupling to the support material.

* * * * *